US 8,591,440 B2

(12) United States Patent
Logue et al.

(10) Patent No.: US 8,591,440 B2
(45) Date of Patent: Nov. 26, 2013

(54) DEVICES AND METHODS FOR ADJUSTABLE FOOT CORRECTION

(75) Inventors: John D. Logue, Baltimore, MD (US); Lew C. Schon, Baltimore, MD (US); Christopher P. Chiodo, Walpole, MA (US); Brent G. Parks, West Friendship, MD (US); David C. Hargrave, Madison, NJ (US); Nick Grippi, Summit, NJ (US)

(73) Assignee: DJO, LLC, Vista, CA (US)

( * ) Notice: Subject to any disclaimer, the term of this patent is extended or adjusted under 35 U.S.C. 154(b) by 1611 days.

(21) Appl. No.: 11/254,544

(22) Filed: Oct. 19, 2005

(65) Prior Publication Data

US 2006/0178606 A1 Aug. 10, 2006

Related U.S. Application Data

(60) Provisional application No. 60/620,044, filed on Oct. 19, 2004, provisional application No. 60/655,675, filed on Feb. 23, 2005, provisional application No. 60/709,675, filed on Aug. 18, 2005.

(51) Int. Cl.
*A61F 5/00* (2006.01)
*A61F 13/00* (2006.01)

(52) U.S. Cl.
USPC .................. 602/13; 602/23; 602/27; 602/65; 602/66

(58) Field of Classification Search
USPC ..................... 602/13, 65–66, 16, 3, 5, 23–29; D24/192; 36/140
See application file for complete search history.

(56) References Cited

U.S. PATENT DOCUMENTS

| | | | | |
|---|---|---|---|---|
| 2,358,966 A | * | 9/1944 | Einstoss | 602/66 |
| 2,600,957 A | * | 6/1952 | Bartis | 36/153 |
| 3,121,430 A | * | 2/1964 | O'Reilly | 36/154 |
| 4,280,489 A | | 7/1981 | Johnson | |
| 4,628,918 A | * | 12/1986 | Johnson, Jr. | 602/13 |
| 4,630,600 A | | 12/1986 | Spencer et al. | |
| 4,729,370 A | * | 3/1988 | Kallassy | 602/65 |
| 4,878,504 A | * | 11/1989 | Nelson | 602/27 |
| 5,050,620 A | | 9/1991 | Cooper | |
| 5,288,286 A | * | 2/1994 | Davis | 602/6 |
| 5,348,530 A | | 9/1994 | Grim et al. | |
| 5,354,260 A | | 10/1994 | Cook et al. | |
| 5,366,439 A | * | 11/1994 | Peters | 602/27 |
| 5,431,624 A | | 7/1995 | Saxton et al. | |
| 5,697,893 A | | 12/1997 | Rhenter | |
| 5,776,090 A | | 7/1998 | Bergmann et al. | |
| 5,833,639 A | | 11/1998 | Nunes et al. | |
| 5,843,010 A | * | 12/1998 | Bodmer | 602/27 |
| 5,885,236 A | | 3/1999 | Varn | |
| 5,897,520 A | | 4/1999 | Gerig | |
| 6,019,741 A | | 2/2000 | Prieskom | |

(Continued)

OTHER PUBLICATIONS

Product Offering of Phantom Dorsal Night Splint from Medical Specialties, Inc. (Jul. 24, 2009).

(Continued)

*Primary Examiner* — Kim M Lewis
(74) *Attorney, Agent, or Firm* — Ropes & Gray LLP

(57) ABSTRACT

Devices and methods of manufacturing and using the same are provided for treating patients suffering from tendon dysfunction. Certain exemplary brace embodiments contain strapping systems and inflatable cells that are adapted to support the forefoot of the patient.

27 Claims, 17 Drawing Sheets

(56) References Cited

U.S. PATENT DOCUMENTS

| | | | |
|---|---|---|---|
| 6,090,059 | A | 7/2000 | Wasserman et al. |
| 6,322,530 | B1 | 11/2001 | Johnson |
| 6,350,246 | B1 | 2/2002 | DeToro et al. |
| 6,361,514 | B1 * | 3/2002 | Brown et al. .................... 602/23 |
| 6,406,450 | B1 * | 6/2002 | Kowalczyk et al. ............. 602/27 |
| 6,602,215 | B1 * | 8/2003 | Richie, Jr. ........................ 602/27 |
| 6,682,497 | B2 | 1/2004 | Jensen et al. |
| 6,755,798 | B2 * | 6/2004 | McCarthy et al. ............... 602/13 |
| 6,860,864 | B2 | 3/2005 | Meyer |
| 6,929,617 | B2 | 8/2005 | McCormick et al. |
| 7,115,105 | B2 * | 10/2006 | Cropper ............................ 602/27 |
| 7,662,117 | B2 * | 2/2010 | Parizot .............................. 602/5 |
| 2003/0153857 | A1 | 8/2003 | McCarthy et al. |
| 2008/0208094 | A1 | 8/2008 | Gaylord |

OTHER PUBLICATIONS

Product Offering of Dorsal PF Night Splint from Amazon.com (Jul. 29, 2009).

Ossur Night Splint Instructions for Use (2009).

* cited by examiner

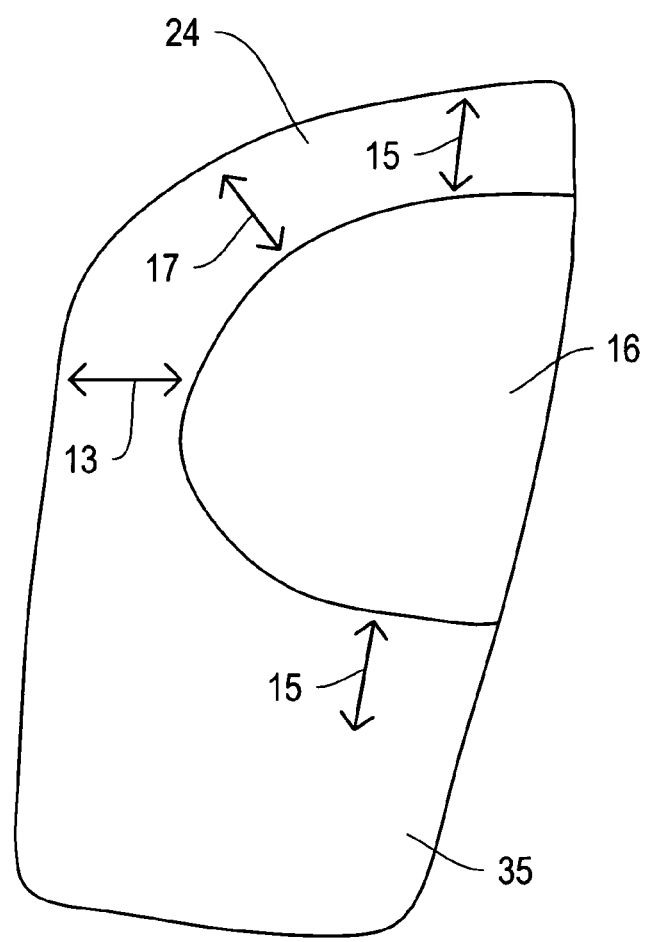
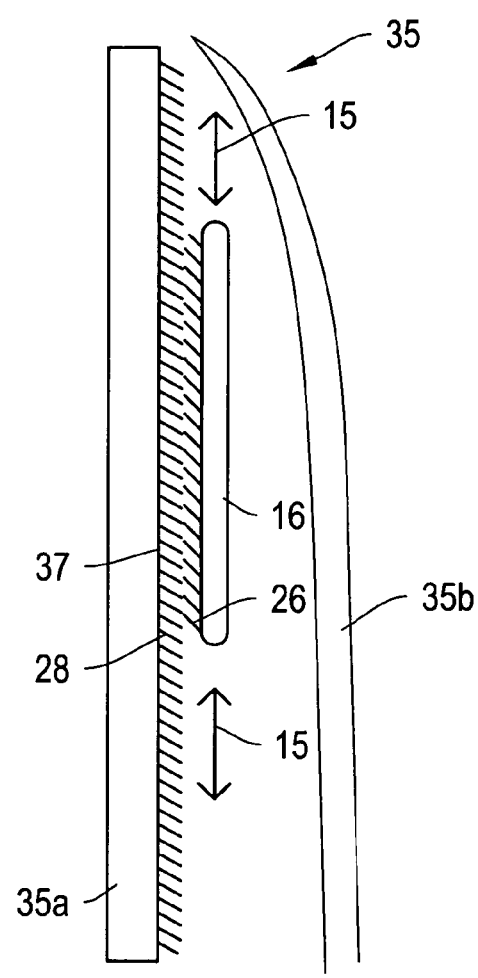
FIG. 3A
FIG. 3B

DEVICES AND METHODS FOR ADJUSTABLE FOOT CORRECTION

REFERENCE TO RELATED APPLICATIONS

This application claims the benefit of U.S. Provisional Patent Application Ser. No. 60/620,044, filed on Oct. 19, 2004, and U.S. Provisional Patent Application Ser. No. 60/655,675, filed on Feb. 23, 2005, and U.S. Provisional Patent Application Ser. No. 60/709,675, filed on Aug. 18, 2005. The teachings of the foregoing applications are hereby incorporated by reference herein in their entirety.

BACKGROUND

Many people suffer from posterior tibial tendon dysfunction (PTTD) and other medial or lateral tendon dysfunctions. Prior devices for applying corrective pressure to a foot or ankle affected by tendon dysfunction have used static implants and other structures and have relied largely on a static pressure application to support the limb. An example of such a device is a foot orthoses, featuring a molded or carved material placed under the foot. These devices apply a constant corrective ground reaction force that may only be adjusted by adding or subtracting material beneath the foot. In many cases, these devices are quite painful for the user and do not provide optimal corrective and other support to the user's foot. Improved devices are needed.

SUMMARY OF THE INVENTION

The invention addresses the deficiencies in the prior art by, in various embodiments, providing improved braces for supporting a user's foot for the treatment of tendon dysfunction. Methods of use and manufacture of such braces are also contemplated. In one representative embodiment a brace is provided with a lateral side portion and a medial side portion, with the two side portions being connected by a bottom portion. The brace includes a first strap that extends from the lateral side portion and beneath the user's foot and is adapted to lift the forefoot of the user as the strap is tightened. The side portions, bottom, and flexible member form a housing for containing rigid side-walls that are adapted to support the user's ankle. In certain embodiments, a flexible member (e.g., Neoprene fabric) is provided to wrap around and support the user's forefoot.

In the representative embodiment, the brace also contains a strapping system for supporting the user's ankle and foot. The strapping system includes a first strap positioned with respect to the brace and adapted to lift the user's forefoot. The first strap is adapted to tighten so as to lift the medial arch of the user upwardly relative to the user's lateral mid-foot region. The first strap may be adapted to affix to the user's foot by extending along the top of the user's foot such that at least part of the strap is positioned at least partially distal to the maleolus, thereby assisting in stabilizing the brace during dorsiflexion by the user. The strap includes a portion adapted to wrap around the posterior region of the user's ankle and fasten to a side section of the medial side portion of the brace. Additional straps may also be used to help secure the brace to the user's foot and ankle. In a representative embodiment, an additional strap is positioned to connect the rear portions of the side supports by extending behind the lower posterior portion of the user's ankle. In certain embodiments, only a single front strap is used.

Accordingly to one implementation, at least one inflatable cell is provided with the brace and is adapted to support the foot of the user. The inflatable cell has a filler material that may include at least one of air, liquid and foam, or other compressible resilient material. A plurality or combination of any of the foregoing filler materials is also contemplated. The inflatable cell is adapted to allow the user to control the level of pressure therein by inflation and deflation mechanisms.

In certain embodiments the inflatable cell is disposed within the bottom portion of the brace so as to be adjustably positionable with respect to such bottom portion, providing the user with flexibility to position the cell along the user's instep, medial arch, or other portion of the foot, as needed to provide optimal fit and desired support. The cell may also be adjustably positionable in the vertical direction—it can be extended to a position along the instep of the foot above the medial arch. In certain embodiments, the bottom portion is constructed as a sleeve having upper and lower portions, and the cell is disposed between the upper and lower portions.

Additional inflatable cells, or bladders, may also be used to further support the user's lower leg, foot and ankle. In certain embodiments one or more of an inflatable heel support, a maleolus support, and side-leg inflatable bladders are provided. The additional inflatable cells may be positionable in any desired location, e.g., on the anterior side of the leg, on the posterior side of the leg, along the shin, along the Achilles, or in any other desired position. In embodiments that employ multiple inflatable cells, the cells may be arranged in fluid communication to provide a dynamic bladder system, and each cell may be configured so as to allow the user to control the inflation and deflation pressure in the cell. In certain embodiments a pump or other inflation source is provided to inflate the bladders. The inflation source may be removable and re-attachable by the user, and may be integrated with at least one of the lateral or side portions.

In certain embodiments the housing is structured to allow the user to apply the brace by inserting the user's heel region into the front region of the brace, while in other embodiments the brace is structured so the user applies the brace by first inserting the toes and forefoot into the rear region of the brace.

Methods of manufacture and use of the braces are also provided. In one aspect, a method is provided supporting a user's instep. The method includes providing a support housing to the user's lower leg, applying a first inflatable cell under the user's medial arch, providing a strap to position the first inflatable cell against the user's medial arch and to lift the user's medial arch relative to the user's lateral arch, and securing the strap to the housing.

Various alternative embodiments and sub-features are also disclosed herein with respect to the braces and methods, as will become apparent in the following description.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting, the scope of the invention instead being defined by the appended claims.

FIGS. 3A-3C depict an inflatable cell that is adjustably positionable within the bottom portion of the brace of FIGS. 1A-1D.

DESCRIPTION OF EXEMPLARY EMBODIMENTS

Figure 1A:
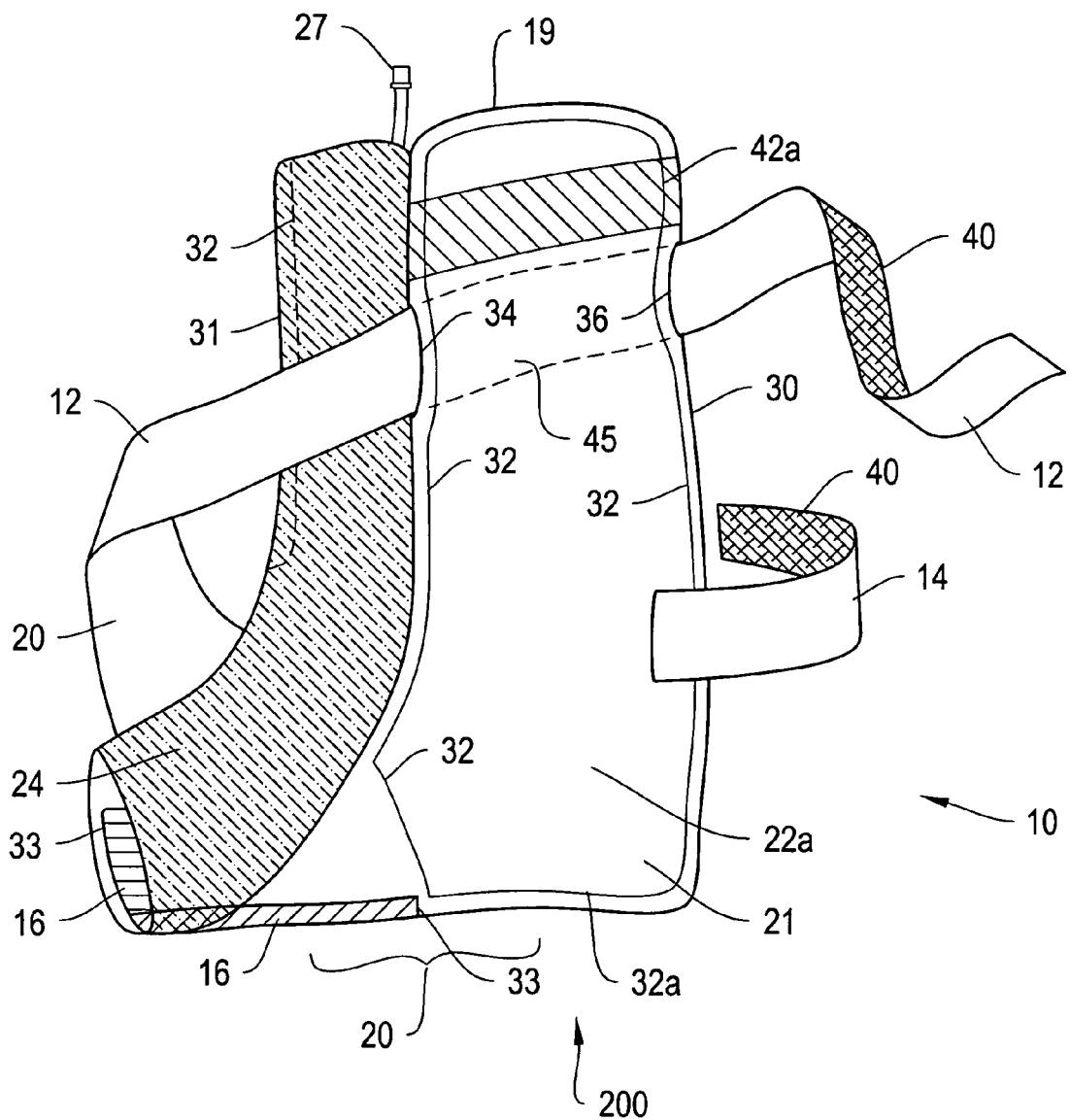
FIGS. 1A-1D depict lateral, medial, bottom, and front views of an embodiment of a brace as disclosed herein.

To provide an overall understanding of the invention, certain illustrative embodiments will now be described, including exemplary embodiments of a device that is adaptable for use in the treatment of a patient suffering from PTTD or other similar condition. However, it will be understood by one of ordinary skill in the art that the devices and methods described herein can be adapted and modified for other suitable applications and that such other additions and modifications will not depart from the scope hereof.

FIGS. 1A-1D depict lateral, medial, bottom and front views of an exemplary embodiment of a brace 10 that fits on the left foot of a patient having a tendon dysfunction. As shown, the brace 10 includes a medial side 100, a lateral side 200, and a bottom portion 35, along with lateral 22a and medial 22b side portions. A strap 20 is provided as an arch support and is affixed to the lower portion of the lateral side 200 (corresponding to the lateral side of a user's side-foot region) and extends underneath the arch region of the foot and up the medial side 100 of the user's foot (the instep). An inflation cell 16 is also provided and is configured to be in functional operation with the bottom portion 35, and is supported against the user's foot as the arch support member 20 is pulled tightly, as described more fully below.

Figure 1B:
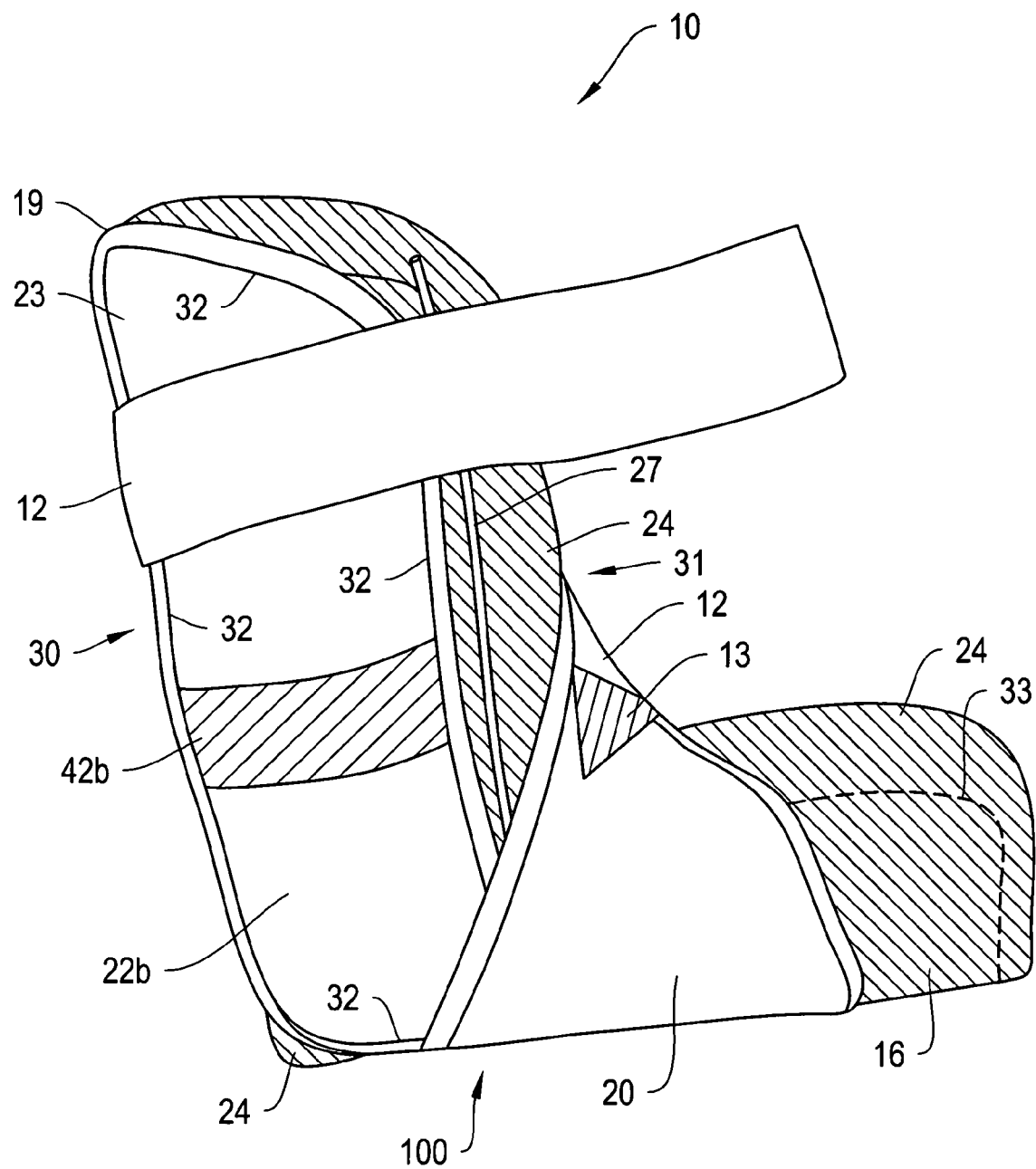

More particularly, FIG. 1A is a lateral view and FIG. 1B is a medial view of the brace 10 having lateral and medial side walls 22a and 22b positioned in the brace 10 so as to provide support for the user's ankle and lower leg. The two side walls 22a and 22b are disposed within a housing 19, which includes flexible casings 21 and 23 adjoined to each other by flexible material 24. The side wall 22a is positioned within flexible casing 21, and side wall 22b is positioned within the flexible casing 23, and each side wall 22a and 22b is positioned so as to extend from the user's heel (in certain embodiments from the bottom of the calcaneous) upward to a position approximately parallel with the user's shin. The depicted side walls 22a and 22b are rigid and may be constructed of laminate, metal, plastic, leather, polymer, aluminum, or other suitable stiff components using rigid or semi-rigid construction. The walls 22a and 22b are also supported and held in place by straps 12 and 14. When strapped in place, the walls 22a and 22b oppose medial and lateral displacement of the user's mid- and hind foot regions. This configuration supports the user's foot and ankle by providing a medial force against the heel from the lateral side 200 of the user's heel, and a lateral force against the heel from the medial side 100 of the heel, to impeded displacement of the heel in the lateral 200 and medial 100 directions.

The casings 21 and 23 of housing 19 each include a dual layer of flexible material that encases the respective rigid members 22a and 22b. The encased rigid members 22a and 22b are secured in place in their respective sides via stitching 32. As described more particularly below, the casing 23 also includes slots 34 and 36 through its dual layer of material for receiving and positioning the strap 12. The casings 21 and 23 are flexible in the depicted embodiment and may be made of nylon, polyester, cotton, or any other suitable fabric. The casings 21 and 23 may also be made of relatively inflexible material, such as a plastic.

Figure 3C:
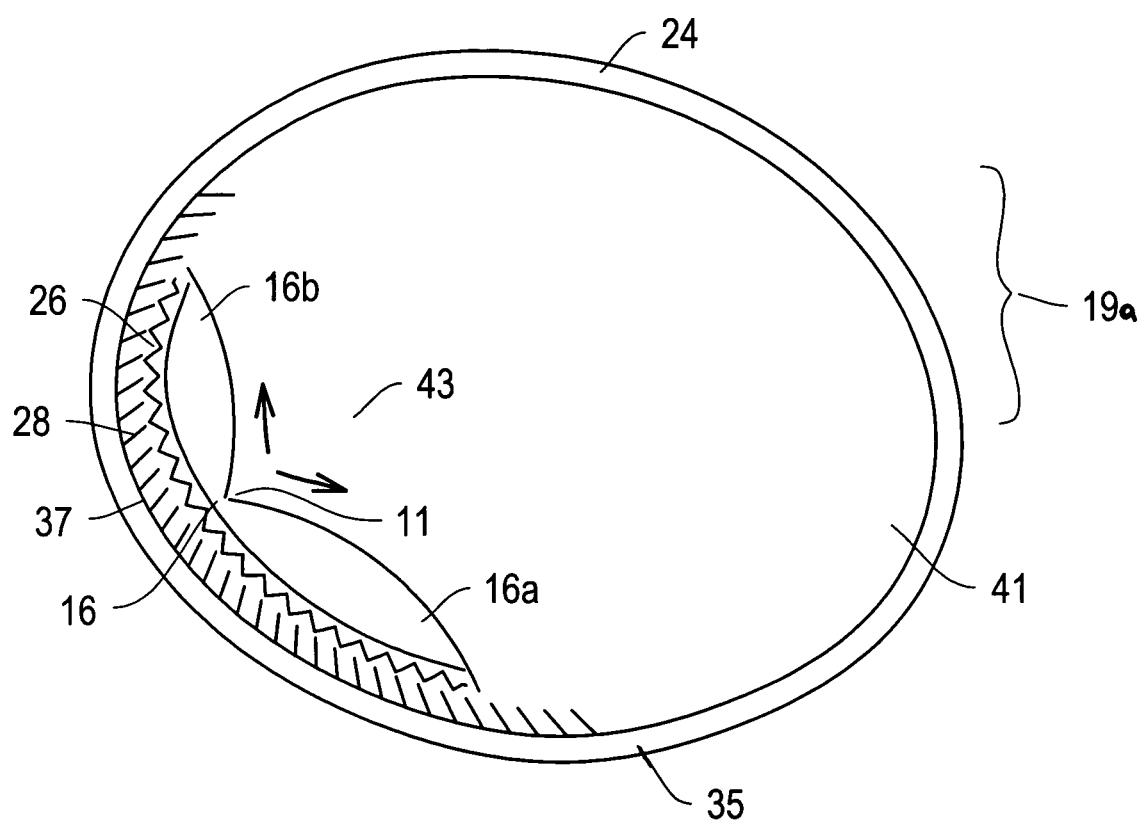

As shown in FIGS. 1A-1D, the flexible material 24 is provided to connect the casings 21 and 23 and to provide support to the anterior region 31 of the brace (corresponding to the fore-region of the user's foot and ankle). In certain implementations, such as is shown in FIG. 3C below, the flexible material 24 may be configured to form a contiguous layer of material with bottom portion 35. Moreover, the material 24 may be made of any suitably flexible material, such as Neoprene or other stretchable fabric. Other examples of suitable flexible material 24 may be found in U.S. Pat. No. 6,755, 798 (McCarthy and Hargrave).

Figure 1C:
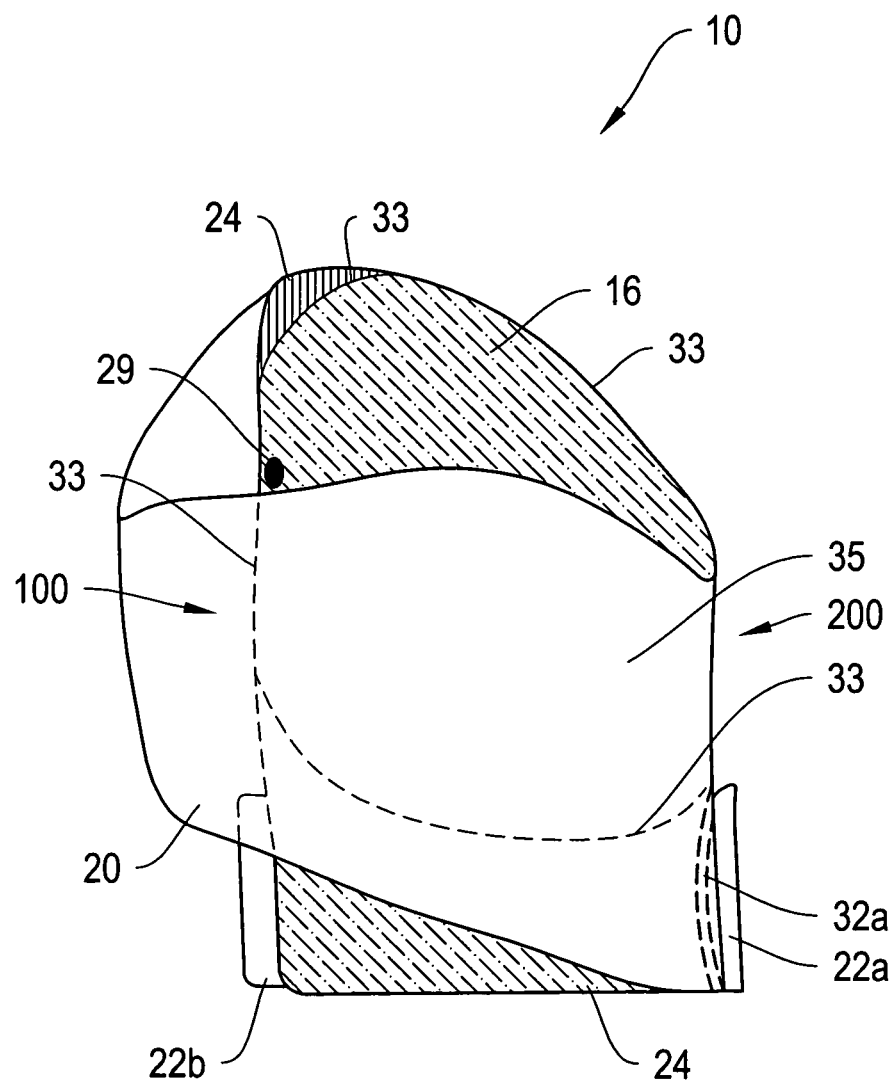
Figure 1D:
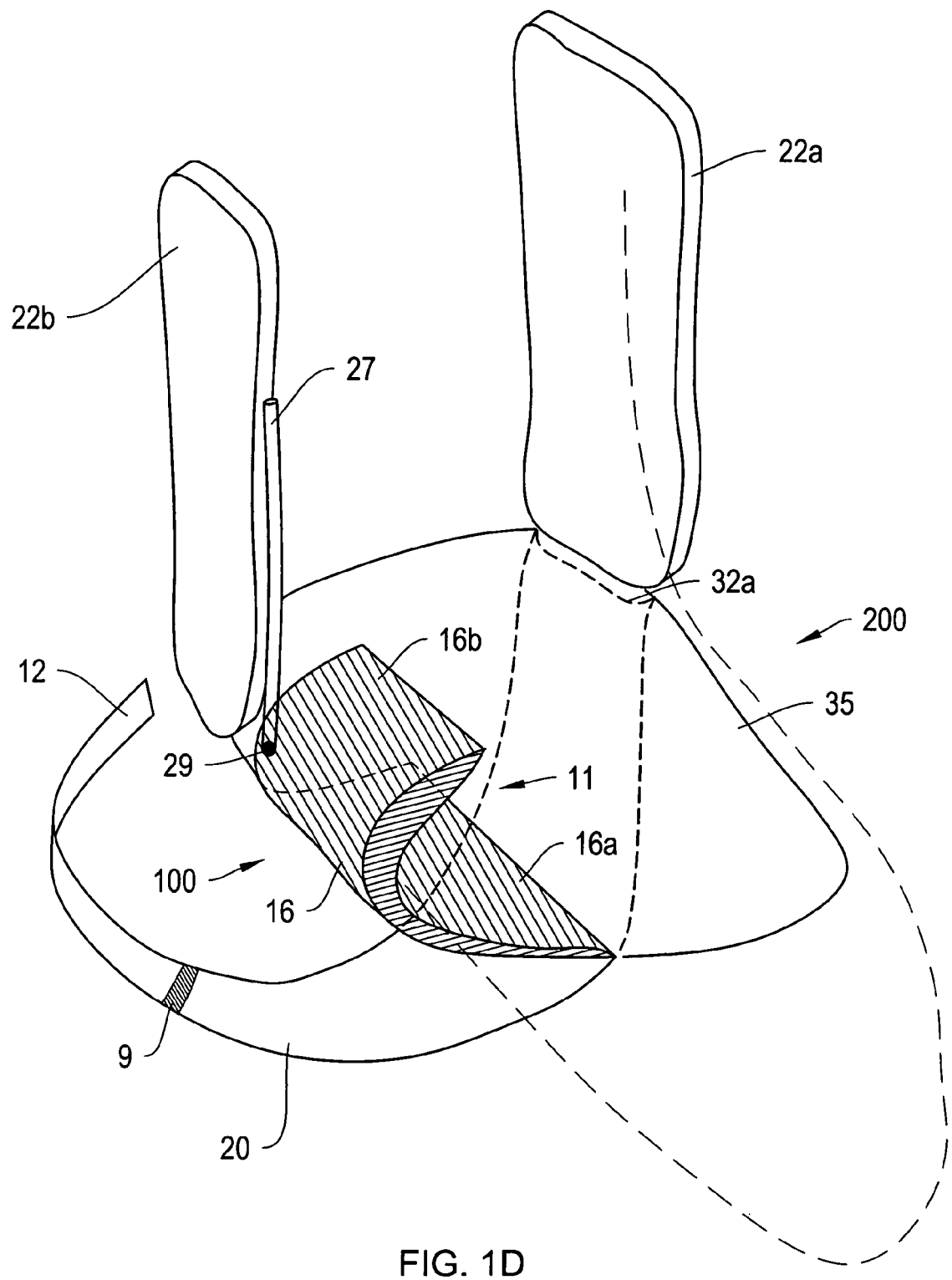

As noted above, the brace 10 includes an arch support member 20 to lift the forefoot, particularly the arch region of the user's foot. FIG. 1C is a bottom view of the brace 10 and depicts support member 20 anchored to lateral portion 200 of the bottom region 35 and wrapped loosely about medial portion 100 of the bottom region 35 of the brace 10. In the depicted embodiment, the support member 20 is formed from an extended piece of the fabric used to form casing 23 and is anchored to the lower lateral portion 21 of the housing 19 by a portion 32a of the stitching 32 that fastens the rigid wall 22a within the casing 23. The stitching 32 (including 32a) may be substituted or used in combination with any other suitable connecting mechanism, such as Velcro, hook and loop fastener, adhesive, zipper and other mechanical fasteners, magnets, welding, imbedding processes or any other suitable mechanism. The arch support member 20 may be made of any suitable polymer or other flexible material that will allow the member 20 to be pulled tight under the bottom region of the user's foot. The member 20 may include stretchable fabric, and it may also be adapted to include a water resilient material on one or more of its sides to assist in regulating the flow of moisture from the patient's foot and lower leg.

The arch support member 20 further includes strap portion 12 to form a strapping system for securing the brace 10 to the user's foot. The strap 12 wraps around the user's ankle and tightens to secure the member 20 to the foot and ankle. The strap portion 12 may be a continuous tapered or untapered extension of support member 20, or may optionally be affixed to the support member 20 by connecting member 9. Connection 9 may be formed by sewing the fabric of member 20 to strap 12, or by any other suitable mechanism such as Velcro, zipper or other mechanical attachment, adhesive, magnets, welding, embedding processes, or other suitable mechanism. As described more fully below, in reference to FIGS. 6A-7B and FIG. 9, the strap 12 is adapted to strap across the top of the user's foot in a position that is at least partially distal to the maleolus, thereby securing the brace 10 during dorsiflexion of the user's ankle.

In operation, the strap 12 is tightened to pull the arch support member 20 tightly against the bottom region of the brace 35 (corresponding to the bottom region of the user's foot), thereby lifting the arch region (e.g., the medial arch region) of the foot vertically to provide therapy to a user suffering from tendon dysfunction. The tightening occurs as the strap 12 is pulled through a slot 45 having ends 34 and 36 of casing 23. The slot 45 is positioned within the casing 23 at an angle (for example, about 10 to about 45 degrees with the horizontal). As the user pulls strap 12 through ends 34 and 36, the pulling is directed along the angled plane of the strap 12, which directs the user's pulling force of member 20 in a vertical direction with respect to the base of the user's instep to tighten the strap 12 and member 20. In certain embodiments, this tightening mechanism by the strapping system lifts the instep or medial arch of the user relative to the corresponding lateral position of the user's midfoot. In practice, the lifting increases the height differential between the user's medial arch and the user's lateral arch. The user may wear the brace 10 in this strapped configuration to lift the medial arch relative to the lateral mid-foot, and maintain the lifted configuration, for a week, or a month or even years. In this respect, the brace 10 may be adapted to support and, with continued use of the brace 10 over time, even correct a fallen instep of a user who is suffering from tendon dysfunction.

Figure 2:
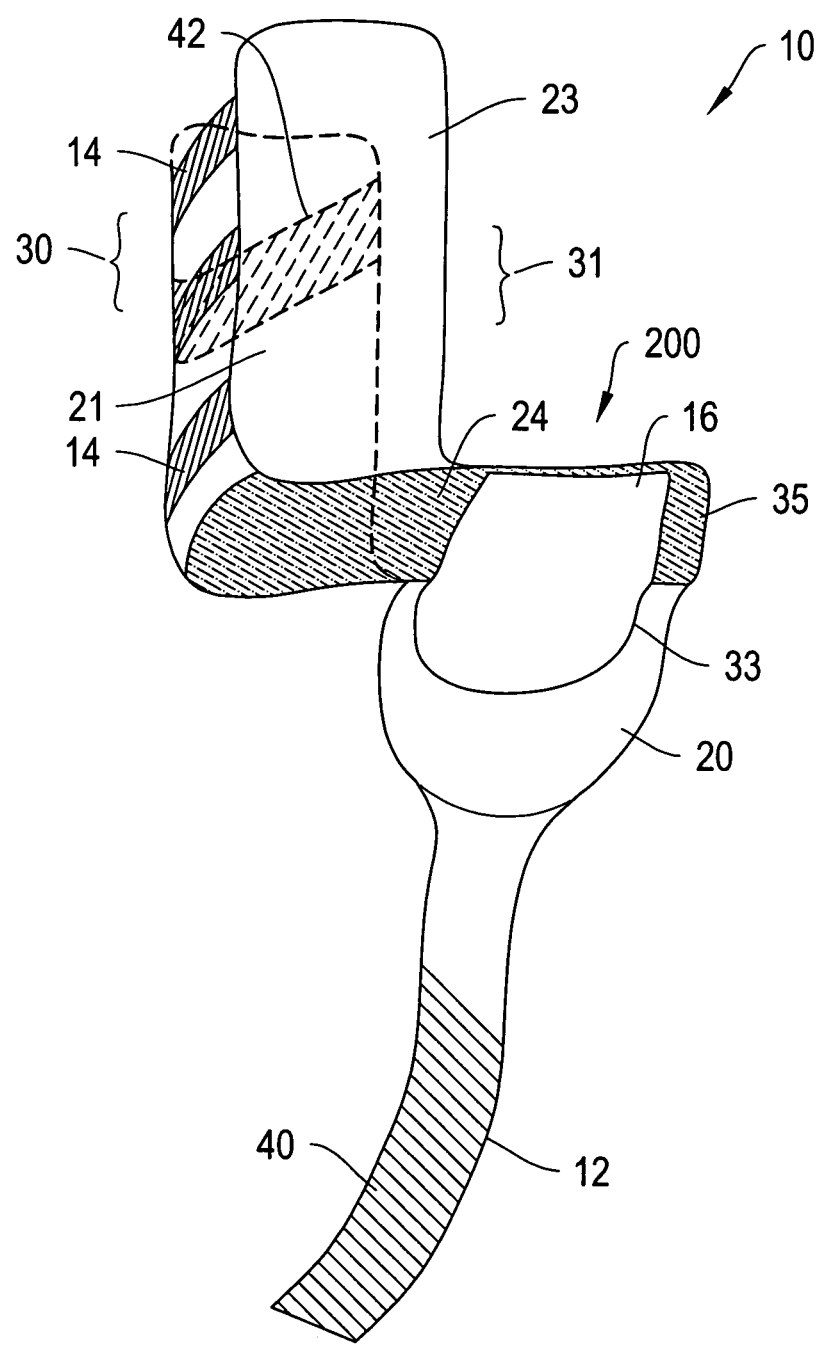
FIG. 2 depicts an embodiment of a brace having a single-front strapping system.

As shown in FIG. 1A, the strap 12 is adapted to wrap around the rear region 30 of the user's lower leg and be secured around the shin and Achilles region of the user by the attachment of Velcro region 40 to region 42a. Strap 14 may optionally be used to further secure the side walls 22a and 22b against the rear region of the user's leg. The strap 14 is positioned roughly parallel with the horizontal (although it may also be positioned at an angle if desired). While multi-strap embodiments are described above, single-strap systems may also be used to help secure the brace to the user's foot and ankle. FIG. 2 depicts an example of a front-loading brace similar to the embodiment of the brace 10 described above, but wherein the brace 10 of FIG. 2 is adapted to allow the user to affix the brace 10 to the user's foot by the use of only a single-front strap 12. The brace 10 of FIG. 2 includes rigid side-walls 22a and 22b interfitted with bottom region 35 (formed of flexible material 24, as described above) and inflatable cell 16 adjoined to bottom region 35. A plurality of straps 14 are optionally included along the posterior region 30 of the brace 10 to receive the user's leg. In operation, the user of this single-strap model of FIG. 2 inserts the heel through the anterior region 31 of the brace and into position adjacent the straps 14 of rear region 30. The arch support member 20 is then pulled upwardly through the use of strap 12 so as to lift the instep of the user, and wrapped over the navicular region of the foot. The strap 12 wraps around the lateral portion 200 of the brace, then around the rear portion 30 and finally applied along the medial portion 100 to connect strap 12 to Velcro region 42 by Velcro attachment 40. In one exemplary embodiment, only the single-front strap 12 is used to fix the brace 10 to the user's foot and the rear straps 14 are not included.

The brace 10 further includes an inflatable cell 16 that is positionable along at least a portion of the arch of the user's foot and is adapted to cushion and otherwise support the user's foot. As shown in FIGS. 1A-1D, the inflatable cell 16 interconnects with the bottom portion 35 of the brace 10 and the arch region of the brace 10 by stitching 33 and is positioned to fit under one or more of the forefoot, lateral mid-foot (such as the lateral arch) and medial arch region of the user's foot to cushion and support the foot for corrective and therapeutic uses. As shown particularly in FIG. 1D, which depicts the brace 10 of FIGS. 1A-1C without the flexible material 24, the cell 16 includes a lower portion 16a positioned under the user's foot, e.g., under the medial arch, and connected to the bottom region 35 of the brace 10, and an upper portion 16b positioned with respect to the brace 10 so as to support the upper medial arch of the user's foot.

In the depicted embodiment, the cell 16 is stitched to the lower region of the brace 35 and to the flexible material 24 by stitching 33. In alternative implementations, the cell 16 may be attached within the housing 19 of the brace in a releasable and adjustable manner. FIGS. 3A-3C depict exemplary mechanisms for adjustably positioning the cell 16 within the brace 10 (and, hence, with respect to the user's foot) as desired by the user. More particularly, FIG. 3A depicts a bottom view of the brace 10, and FIG. 3B depicts a side view of the bottom portion 35 of the brace 10, each with the arch support member 20 removed. As shown in FIG. 3A, a user can adjust the position of cell 16 within the bottom region 35 forward and/or backward in the longitudinal direction 15 in respect to the bottom portion 35 of the brace 10. The longitudinal adjustment occurs by disengaging the attachment between regions 26 and 28, adjusting the cell 16 longitudinally in the desired position with respect to region 35, according to direction arrow 15, and then re-forming the attachment between regions 26 and 28. The cell 16 may similarly be adjustably positioned in the horizontal direction, as shown by direction arrow 13. The cell may also be angularly adjusted in any other direction, e.g., direction 17, with respect to the bottom region 35.

Similarly, in certain exemplary configurations, the cell 16 can be axially rotated and accordingly adjusted within the housing 19 of the brace 10. FIG. 3C depicts a front portion 19a of the housing 19 of the brace 10 and a close-up depiction of region 41 through which the user's toes will protrude when the brace 10 is worn. The cell 16 and the upper side 37 of the lower portion 35 of the brace 10 have Velcro mating regions 26 and 28. To axially adjust the cell 16, the Velcro regions 26 and 28 are disengaged, the cell 16 is axially positioned within the housing 19 in the directions indicated by direction arrow 43, and the Velcro regions 26 and 28 are then reformed.

The adjustable mechanisms can also be combined with other protective configurations to receive and cover the cell 16. As shown in FIG. 3B, the bottom region 35 is configured as a sleeve that includes a lower layer 35a and upper layer 35b, the upper layer 35b being positionable against the bottom of the user's foot. The cell 16 is disposed between the lower layer 35a and upper layer 35b and is adjustably positionable between these two layers 35a and 35b. Similar to the embodiment of FIG. 3C, in the exemplary embodiment of FIG. 3B, the cell 16 and the upper side 37 of lower layer 35a have Velcro mating regions 26 and 28, respectively, that join together to hold the cell 16 in place within the bottom region 35. This joining of the cell 16 via mating regions 26 and 28 allows the user to securely position the cell 16 at the desired location within the sleeve 35. In an alternative configuration, similar to that shown in FIG. 3C, the bottom region 35 is only a single layer 37 with Velcro mating region 28, and the mating region 28 is adapted to join with mating region 26 on the cell 16.

While the depicted embodiments of FIGS. 3A-3C use a Velcro attachment mechanism for adjoining cell 16 to the bottom region 35 of the brace 10, any other releasably attachable mechanism can be used to effect the positioning, such as tape, releasable polymer, zipper or other mechanical mechanism, or any other suitable approach. Through the use of the adjustability configurations the brace 10 is adaptable for use with persons of differing foot sizes and of differing pain points within the foot by positioning the cell 16 within the bottom portion 35 to fit comfortably under the user's arch.

The cell 16 may be sized and shaped as desired. For example, as shown in FIGS. 1A, 1B, 1D, and 3C, the cell 16 may be sized such that portion 16a extends vertically above the medial arch of the user's foot to a point along the instep above a region 11 corresponding to the vertical middle portion of the arch. Alternatively, the portion 16a may be limited in size to closely fit the medial arch but not substantially extend beyond the perimeter of the medial arch. The cell 16 may also be configured to be positioned around the perimeter of the medial arch.

The inflatable cell 16 may be constructed from polymer or any suitable material that is adaptable to receive an inflation medium. The cell 16 includes an inflatable support component such as a foam pad, an air cell, a liquid cell such as water, gel or other liquid, or other suitable structure. Examples of inflatable components that may be used are found in U.S. patent application Ser. No. 10/726,343 (entitled "Orthopedic Appliance with Moisture Management System" by Johnson et al.). Other examples are found in U.S. Pat. No. 6,755,798 (by McCarthy and Hargrave).

Figure 4:
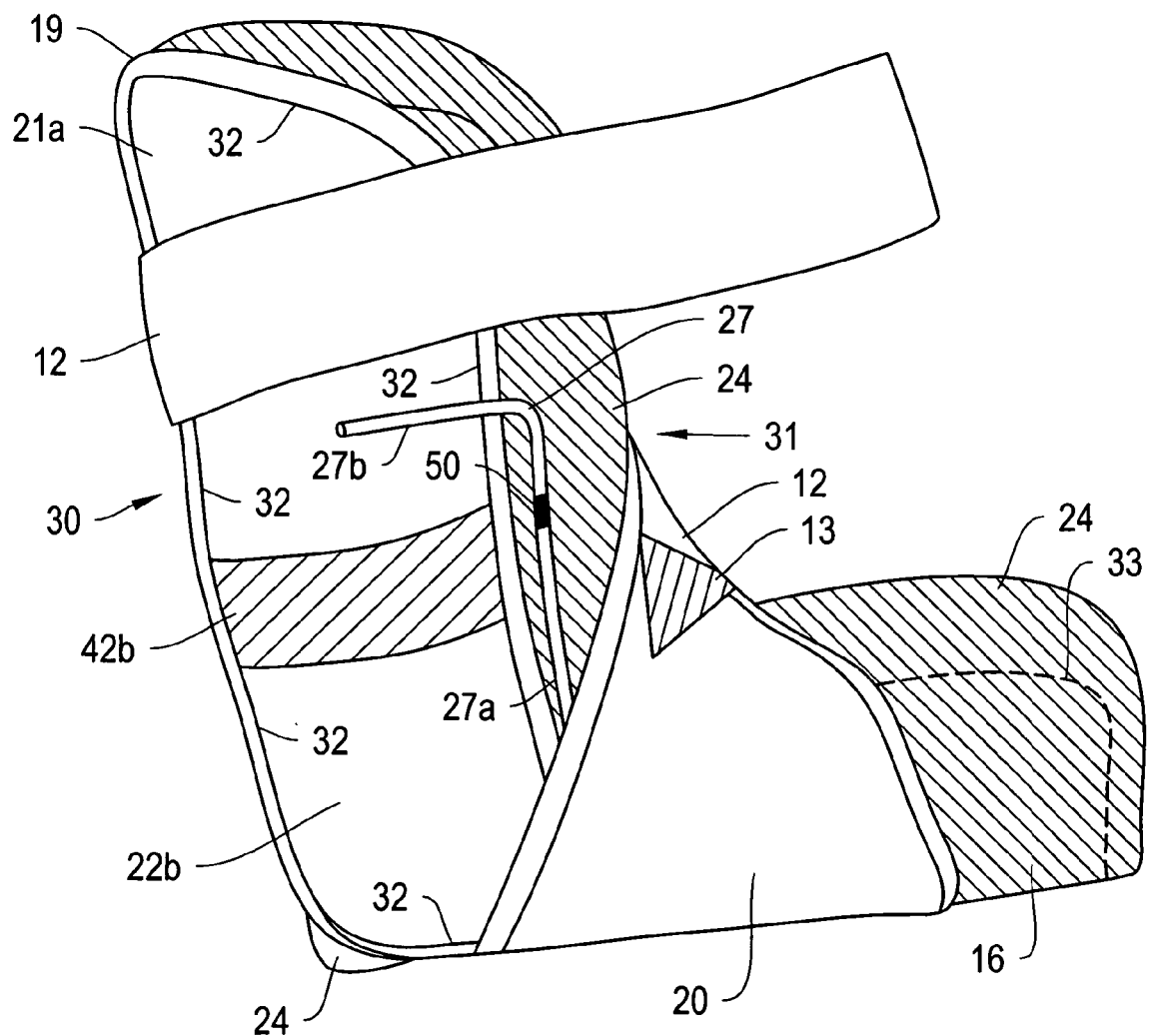
FIG. 4 depicts an embodiment of the brace of FIGS. 1A-1D having an alternative bent configuration for an inflation tube.

Referring again to FIGS. 1A-1D, the exemplary brace 10 includes an inflation port connection tube 27 that connects to the arch cell 16 via an inflation port 29 to allow the user to inflate or deflate the cell 16. As shown in FIG. 1A, the connection tube 27 is positioned vertically so as to extend along the shin region of the user. FIG. 4 is an alternative embodiment of a brace 10 having a tube 27 that has lower segment 27a and upper segment 27b and is positioned such that a lower segment 27a of the tube 27 extends vertically from its connection with the inflation port 29 within cell 16 and then bends, with an angled extension 27b, by which the tube 27 is adapted to extend parallel to the ground for comfort and convenience. Any other desired configuration may be used. A valve 50, such as is described below with reference to FIGS. 5A-5E is also placed in the tube 27 to allow the user to regulate fluid flow through the tube 27.

The brace 10 is adapted to allow the user to inflate and deflate the cell 16 through a hand-held (or automated) inflation source. As described below with reference to FIG. 10, a bulb 51 may be connected to the tube 27 and may be compressed in a direction toward the user's leg, thereby causing air to flow through tube 27 to inflate the cell 16. The release of bulb 51 from the compressed position allows ambient air to re-fill the bulb 51, which renders the bulb 51 available to compress again and continue to fill the cell 16. Any other suitable electrical or manual pump or other inflation device may be also used.

Through use of the inflation device 51, the user inflates the cell 16 to a desired pressure. The inflation device 51 may also be integrated with a control device for controlling the inflation level. For example, FIGS. 5A-5E depict a one-way valve 50 that can be inserted into the tube 27 to control the inflation pressure of cell 16 (and any other cell described herein). The valve 50 includes an inner flap 56 having upper flap portion 56a and lower flap portion 56b, such portions being adapted to open and close to facilitate fluid flow through the valve 50. FIG. 5B depicts the flaps 56a and 56b in closed position. In one exemplary application, the valve 50 is inserted into the tube 27 between portions 27a and 27b (as described above with reference to FIG. 4). In this example, the closed flaps 56a and 56b of FIG. 5B operate to prohibit fluid 58 from flowing back from tube 27a to tube 27b, while FIG. 5C depicts the flaps 56a and 56b in open position to allow fluid 58 to flow from the upper tube 27b to the lower tube 27a. The flaps 56a and 56b are adapted to open when the fluid pressure in the upper tube 27b is balanced with or exceeds the pressure in the lower tube 27a, which may be accomplished, for example, by pumping the inflation device 51 shown in FIG. 6B, as necessary.

Figure 5A:
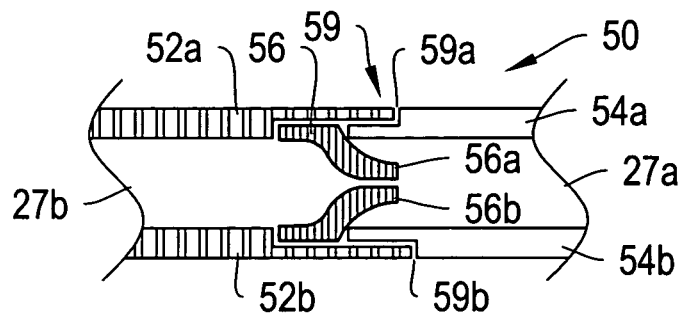
FIGS. 5A-5E depict an embodiment of a pressure valve and its fluid flow functionality, as may be used with any of the brace embodiments disclosed herein.
Figure 5B:
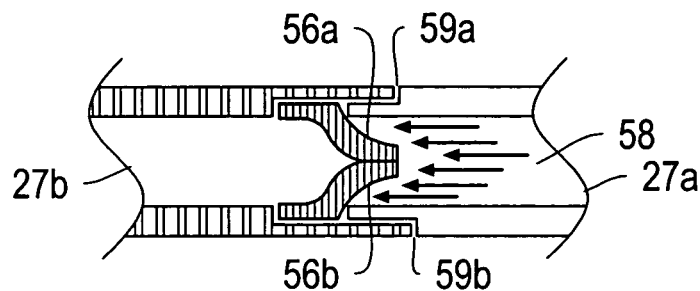
Figure 5C:
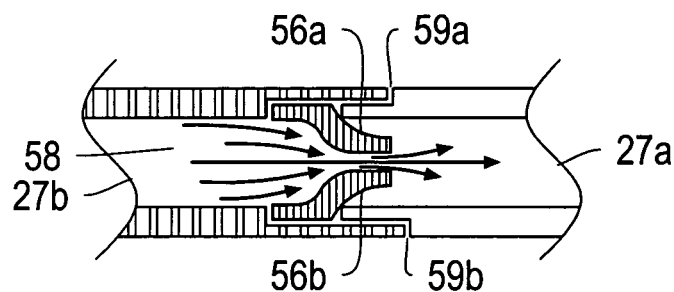
Figure 5D:
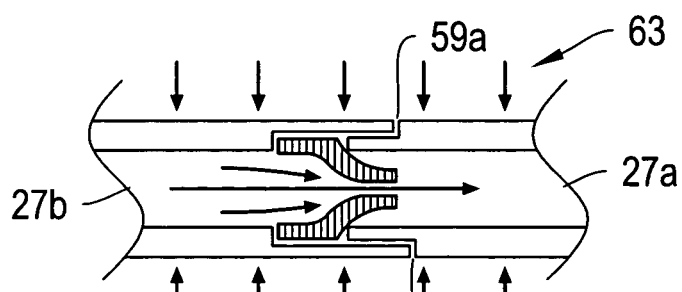
Figure 5E:
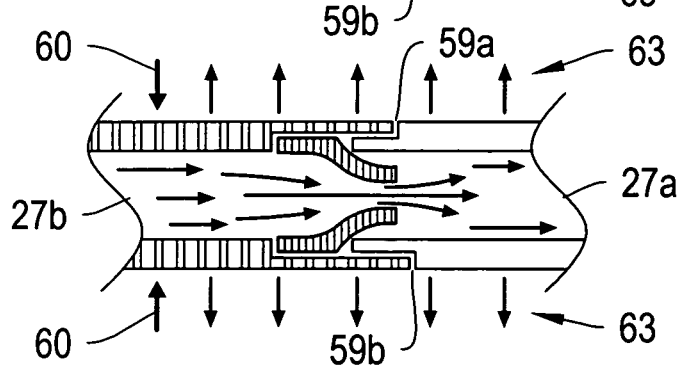

The valve 50 is shown in cross-section in FIG. 5A as having upper side 52a and lower side 52b, which would mate with tube portion 27b in a fluid-tight seal. Similarly, upper side 54a and lower side 54b mate with tube portion 27a in a fluid tight seal. The two upper sides 52a and 54a also mate, as do the two lower sides 52b and 54b, in tongue-and-groove joint 59, such joint 59 being depicted in FIGS. 5A-5E as having upper region 59a and lower region 59b. As shown in FIG. 5D, tongue and groove joint 59 is closed to form a fluid-tight seal around the valve 50, thereby prohibiting air 63 from flowing into (or out of) the sides of the valve 50. As shown in FIG. 5E, the valve 50 can also be purged by compressing in the region 60 above the valve flaps 56a and 56b, allowing air 63 to escape from the valve 50 through the regions 59a and 59b of the tongue-and-groove joint 59. The valve 50 can be integrated within any flow tube described herein.

While the embodiments described above depict the use of a single cell 16 in the brace 10, alternative embodiments employ a plurality of cells to form a bladder system for supporting the arch and other regions of the user's lower leg. The brace 110 shown in FIGS. 6A and 6B exemplifies a multi-cell embodiment. The brace 110 is configured similarly to brace 10 shown above in reference to FIGS. 1A-4, having rigid members 22a and 22b positioned on lateral 200 and medial 100 sides of the user's foot. The members 22a and 22b are secured by a strapping system that includes an upper strap 64 and a lower strap 66, with upper strap 64 having an end 64a attached to the medial side 100 of the brace 110 and an end 64b adapted to wrap around an upper portion the front 31 of the user's leg and attach through a Velcro or other attachment mechanism to the end 64a. Similarly, lower strap 66 has an end 66a attached to the lateral side 200 of the brace 110 and an end 66b adapted to wrap around a lower portion of the front 31 of the user's leg and attach through a Velcro or other attachment mechanism to the end 66a, including the arch cell 16, but has an additional inflation cell 68 positioned beneath the heel of the user. The cell 68 is adapted to be in fluid communication with cell 16 through a tube (not shown), such that the inflation and deflation of cell 16 by the use of inflation device 51 or other appropriate mechanisms can be used to inflate and deflate cell 68 to control the pressure in cell 68. As with any other cell described herein, the cell 68 can be sized and shaped as desired to apply to the particular needs of the user.

Figure 6A:
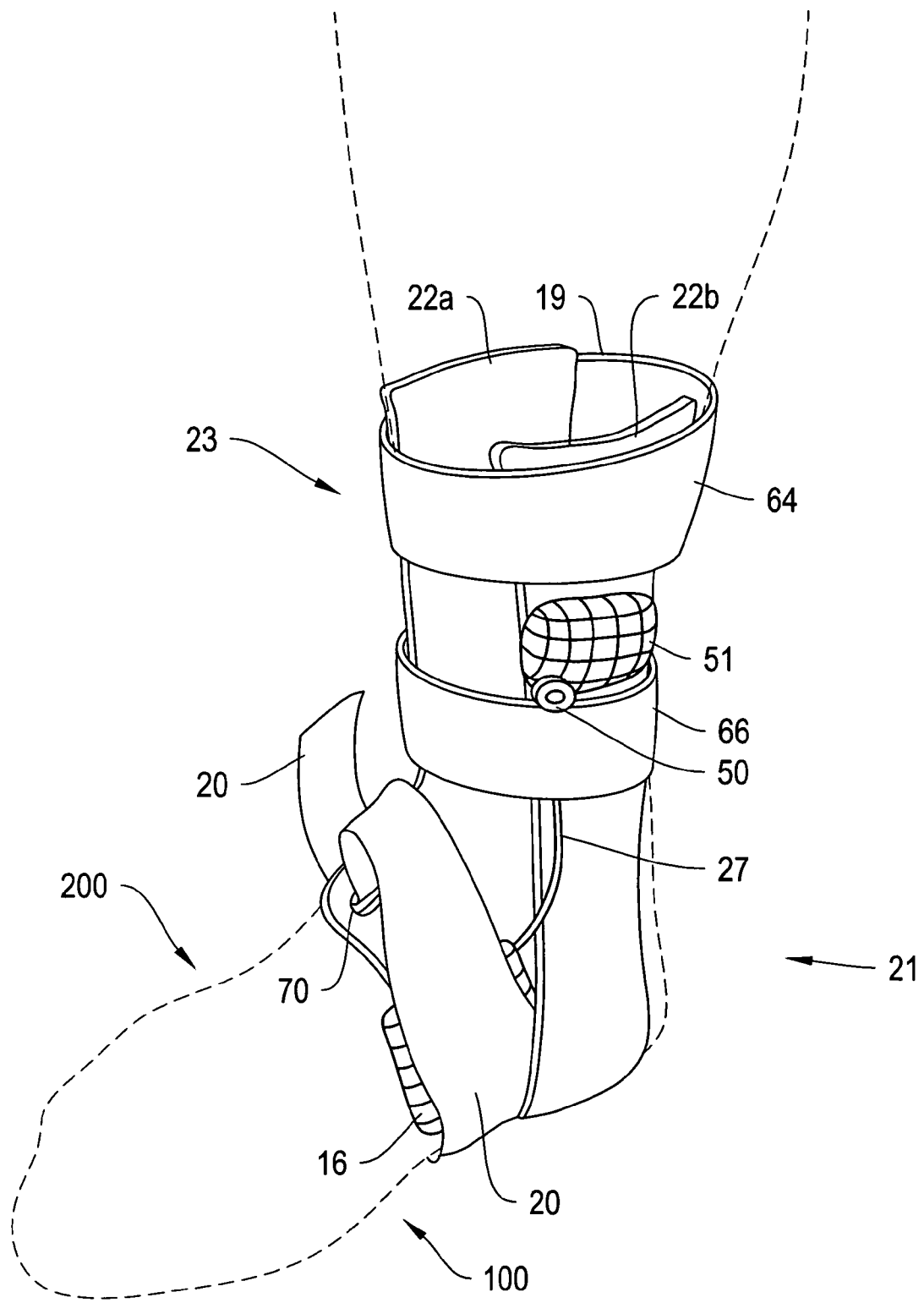
FIGS. 6A-6B depict an alternative embodiment of a brace having a plurality of support cells.
Figure 6B:
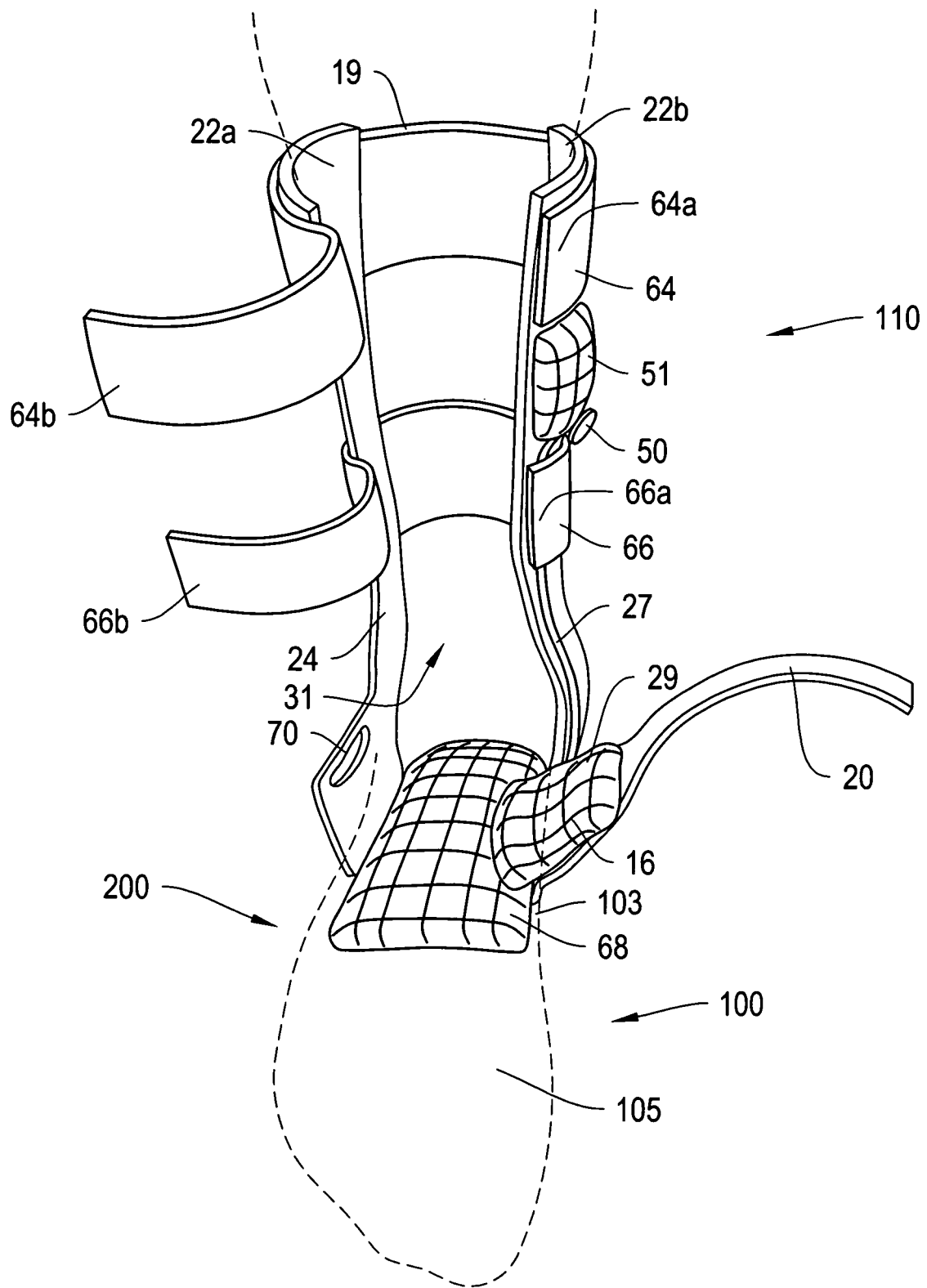

As shown in FIG. 6B, cells 16 and 68 cooperate in assisting the treatment of the patient. As shown, the cell 16 is affixed to support member 20 and strap 12 and extends vertically and medially away from the cell 68. In some embodiments the cell 16 may be positioned to extend perpendicular to the cell 68. Cell 68 is also positioned to support a rear region of the lower arch and the heel region of the hind foot of the user, while cell 16 is positioned to support the fore-region of the medial arch, as described above. To apply brace 110, the user wraps strap 20 over the top region of the foot and inter-fits strap 20 through loop 70, which is located within the lateral portion 200 of the housing 19 of the brace 110. The strapping and inflatable cell systems of FIGS. 6A-6B are adapted to be applied so as to both lift the user's forefoot and cushion the user's instep. Lifting the strap 12 of FIG. 6A vertically lifts the arch support member 20 and thereby lifts the forefoot 105 of the user, as described above with reference to similar structures of FIGS. 1A-1C, while cell 16 combines with cell 68 to simultaneously support the user's heel 101 and medial arch 103.

Figure 7A:
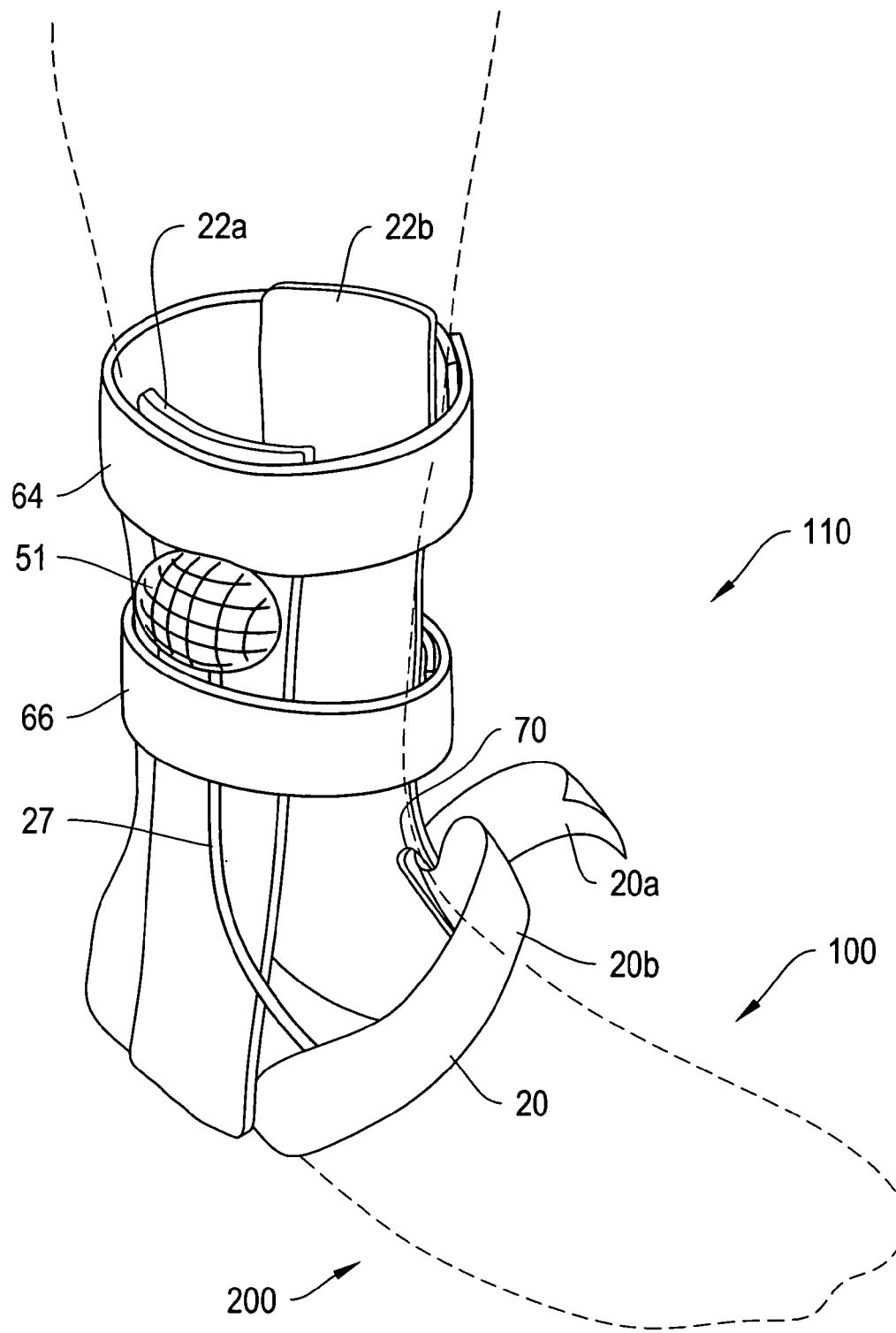
FIGS. 7A-7B depict an alternative embodiment of a brace having a plurality of support cells configured to support both lateral and medial aspects of the user's mid-foot.
Figure 7B:
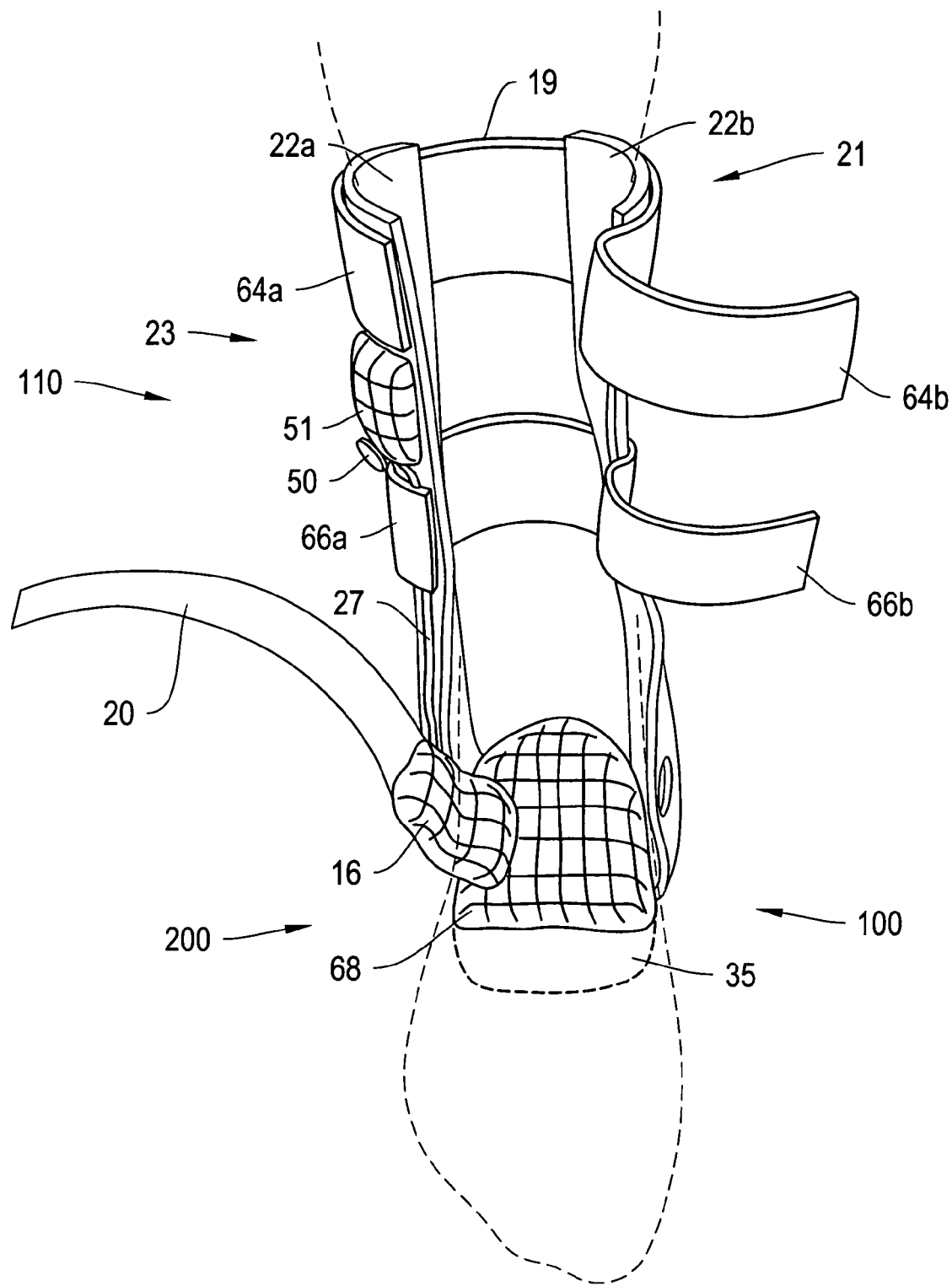

The brace 110 may also be adapted to support the user's forefoot 105 by adjusting the positioning of the lower cell 68 relative to the arch cell 16. FIG. 7A-7B depict the brace 110 of FIGS. 6A-6B having lower cell 68 positioned to fit on the medial side 100 of the lower portion 35 of the brace, thereby supporting the medial arch region of the user. The cell 16 is adjusted to support the lateral side 200 of the user's mid-foot, rather than the medial arch region as shown in FIGS. 6A-6B, by extending away from the cell 68 on the lateral side of the brace 10. Similar to the embodiment shown in FIGS. 6A-6B, the brace 110 of FIG. 7A-7B is affixed to the user's foot by applying strap 20 over the top of the user's foot and into slot 70, then wrapping outer side 20a of strap 20 over top interior side 20b of strap 20 to form a tight connection. This configuration lifts and thereby supports both the medial 100 and lateral 200 regions of the user's mid-foot.

Figure 8A:
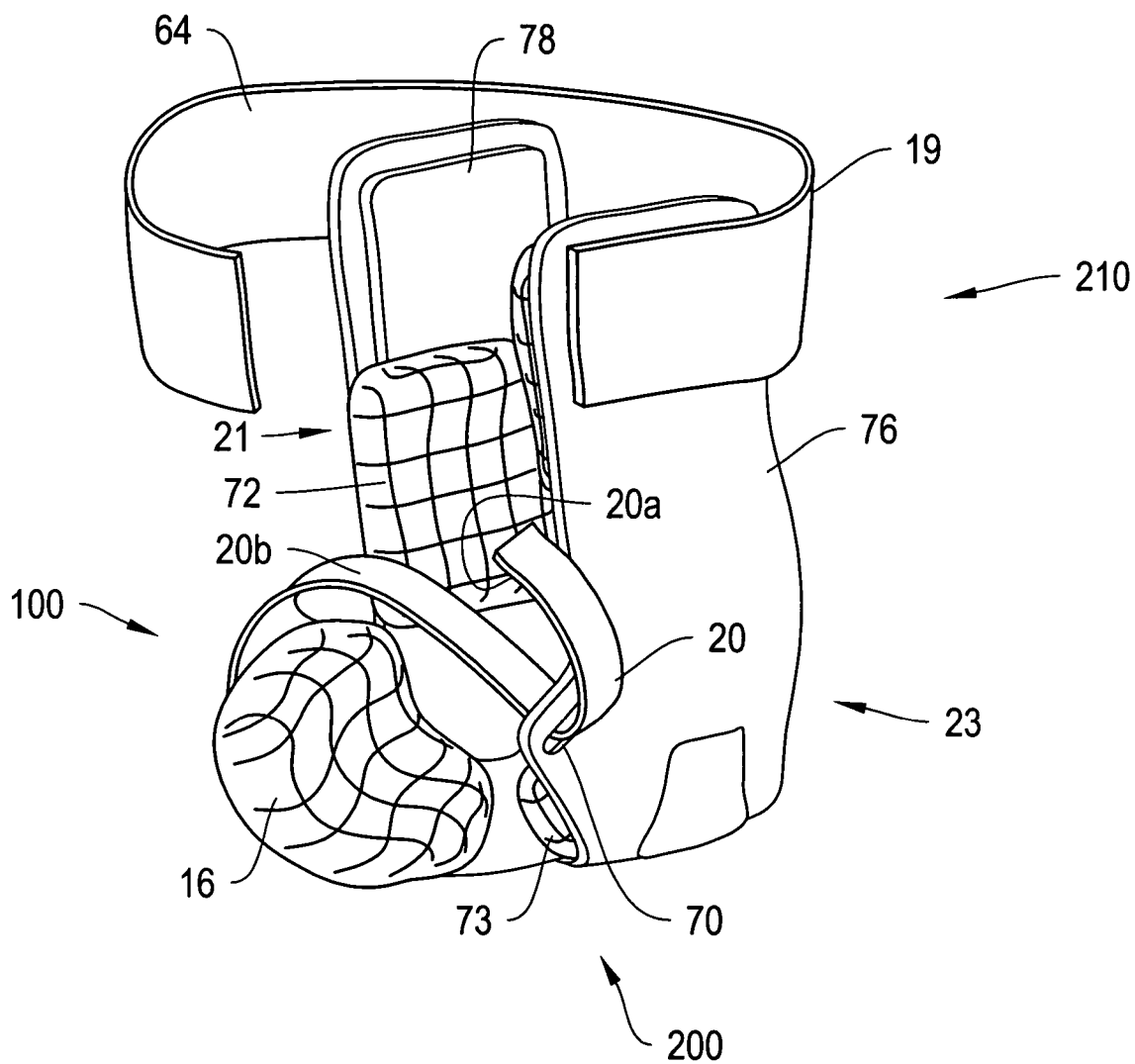
FIGS. 8A-8B depict an alternative embodiment of a brace having an alternative dynamic inflation cell system.
Figure 8B:
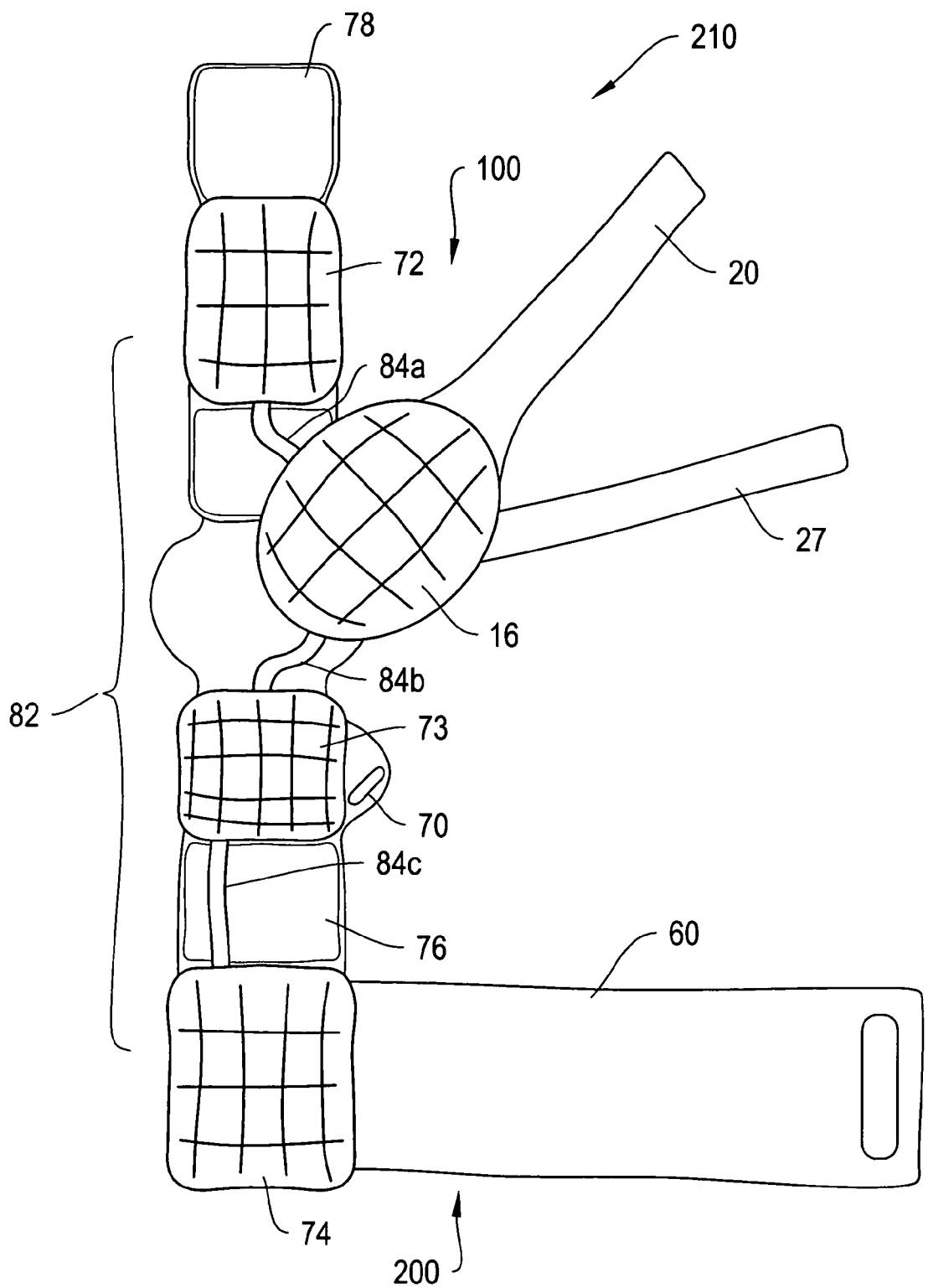

FIGS. 8A-8B depict an alternative embodiment 210 of brace 10 having a plurality of bladders configured in a communicating bladder system. The brace 210 is shown in FIG. 8A as being fully assembled and ready to apply to a foot, while FIG. 8B depicts the brace laid flat. As shown, the brace 210 of FIGS. 8A-8B includes a housing 19 having medial rigid member 78, lateral rigid member 76, and upper strap 64. The brace 210 also includes an inflation bladder 16 adapted to be positioned against and lift the user's medial arch and a strap 20 with inter-fitting components 20a and 20b, as described above in reference to FIGS. 7A-7B. Also included in the brace 210 of FIGS. 8A and 8B are additional inflation bladders that are adapted and positioned to support various aspects of the user's foot and ankle. More particularly, inflatable bladders 73 and 74 are positioned on the lateral member 76 of the housing 19 to support the upper lateral side of the user's leg above the ankle, respectively, while inflatable bladder 72 is positioned adjacent to the medial member 78 of the housing 190 and positioned to support the medial maleolus or other medial aspect of the user's leg. The bladders 72, 73, 74, and 16 are adapted to be in fluid communication through the use of fluid connection ports 84a-84c, forming an inter-connected bladder system 82 that allows the user to adjust the inflation pressure of each of the cells for achieving desired support.

More particularly, as shown in FIG. 8B, bladder 16 is inflatable through fluid conduit 27, as described above with reference to the brace 10. By receiving fluid through conduit 27, bladder 16 pressurizes bladder 72 through conduit 84a and bladder 73 through fluid conduit 84b. Bladder 73 is pressurizable by the user's heel during the user's gait and can thereby pressurize bladder 74 through fluid conduit 84c. The inter-bladder system 82 is also configured to operate by the user's gait, wherein the bladders 72, 73, and 74 are used as pumps to pressurize their respective connecting bladders. For example, when the user bears weight on his of her heel, heel bladder 73 pumps fluid into arch bladder 16 through conduit 84b to pressurize and support the user's arch during the step. Similarly, the pressure added to arch bladder 16 causes fluid to flow into and pressurize maleolus bladder 72 through conduit 84a to further support the ankle. Moreover, the inflation connection ports 84a-84c may be adapted to employ the valve system and structure described above in FIGS. 4A-4E, thereby allowing the user to release the flow of fluid between cells. Moreover, while the bladder 16 is depicted in this exemplary embodiment as being connected to an external inflation source through tube 27, any or all of the bladders 72, 73, and 74 may be similarly connected through an inflation tube, such as tube 27, to an external inflation source.

Figure 9:
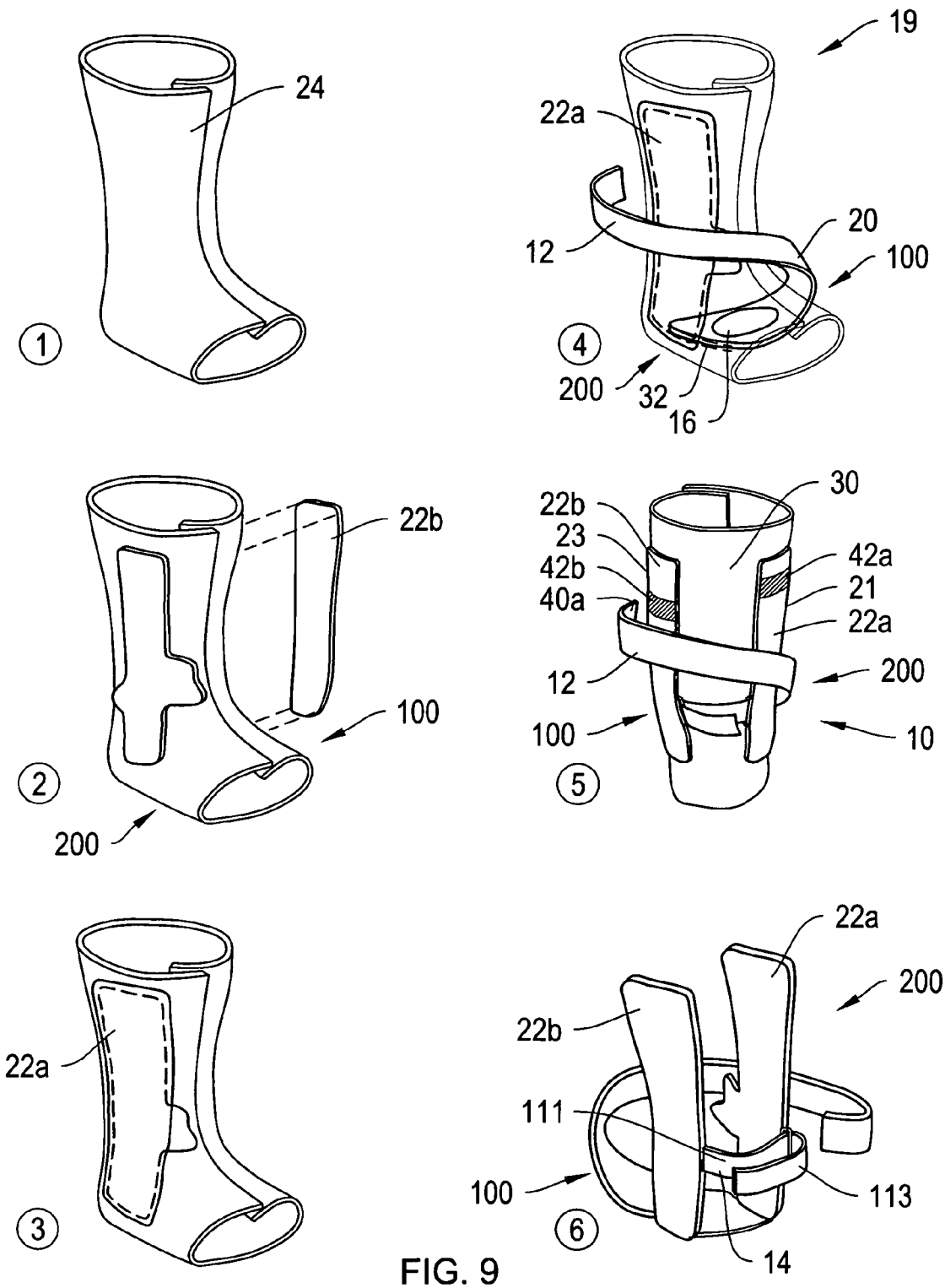
FIG. 9 depicts a process for manufacturing a brace, such as that depicted in FIGS. 1A-1C.

Methods of manufacturing and use of a brace, such as those braces described above, are also contemplated. FIG. 9 depicts a process for manufacturing an exemplary embodiment of a brace, such as the brace 10 described above with reference to FIG. 1A. As shown, in a first step a substantially tubular component 24 is provided and formed of stretchable material as described above.

In a second and third step, side wall portions 22a and 22b are affixed to the tubular portion 24. The side wall portions 22a and 22b may be affixed by any number of suitable methods, for example by gluing, taping, stitching, Velcro, and other mechanisms. The side wall portions 22a and 22b may optionally first be inserted into a flexible pouch such as casings 21 and 23, respectively, as described above and stitched to the tubular portion 24, forming the housing 19. In certain embodiments, the flexible pouch such as casing 21 may also be an extended piece of fabric that can be used as the arch support member 20.

In a fourth step, arch support member 20, having strap 12 and inflatable cell 16, is affixed to the tubular portion 24 of the housing 19.

In a fifth step, two Velcro regions 42a and 42b are affixed to the upper portions of casings 21 and 23, respectively, for receiving the Velcro attachment portions 40 on the strap 12 after it is wrapped around the posterior region 30 of the brace 10. In a sixth step, a lower strap 14 having portions 111 and 113 is affixed to the lateral 200 and medial 100 sides of the brace, with a Velcro attachment mechanism (not shown) for attaching the portions 111 and 113 together. The components 111 and 113 are attachable through a Velcro attachment, which allows the strap 14 to attach securely along the Achilles region 30 of the brace 10.

Figure 10:
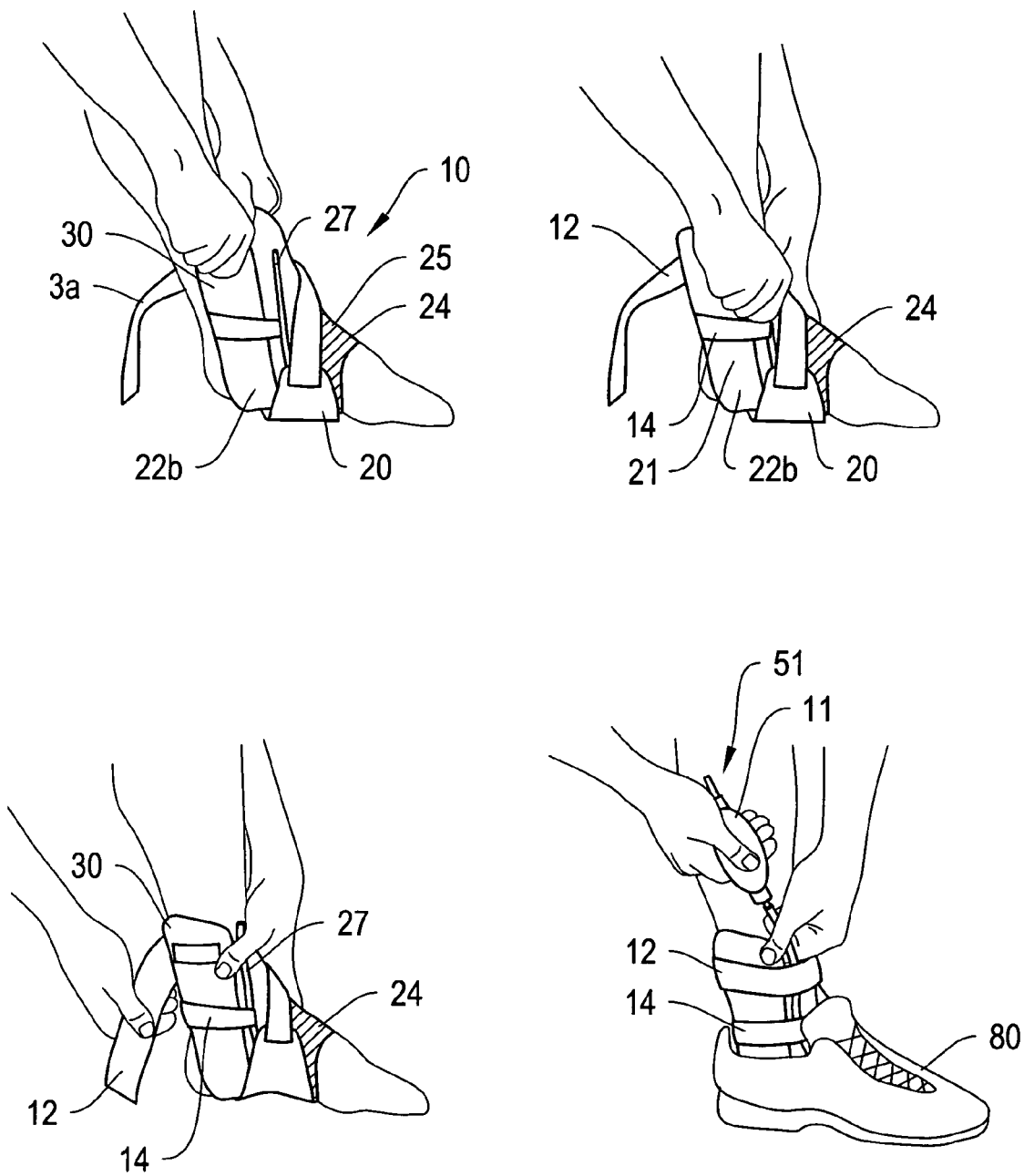
FIG. 10 depicts an exemplary process for applying an exemplary brace to a user's foot, as may be used in the treatment of a patient having posterior a tendon dysfunction.

FIG. 10 depicts an exemplary process for applying a brace, such as the brace 10, to a user's foot, as may be used in the treatment of a patient having tendon dysfunction such as posterior tibial tendon dysfunction (PTTD). As shown, the user positions brace 10 on the user's foot by sliding the foot into the posterior region 30 of tubular portion 24 (shown in this embodiment as being the stretchable material described above). As shown in this FIG. 10, tubular portion 24 includes only a front portion 25 but no rear portion around the posterior region 30 of the brace 10, which leaves the rear portion 30 of the brace 10 open to allow the user to insert the foot through such region 30. The shells referenced in the attached FIG. 10 are similar to the rigid side walls 22a and 22b referenced above.

After applying the brace 10, the user wraps the small strap 14 around the posterior region 30 to anchor the brace 10 in position on the ankle. Next, the user pulls on strap 12 so as to vertically lift the arch support member 20 until it fits snuggly against the instep of the user, thereby vertically lifting the medial arch of the user's foot relative to the lateral mid-foot. After lifting the arch support member 20 to the desired position, the user wraps strap 12 around the upper posterior region 30 of the brace 10 and secures strap 12 to the medial side 100 of the brace 10 by affixing the strap 12 to an attachment region on such side 100, such as a Velcro attachment region 42 similar to that as shown in FIG. 1A. The user then optionally puts on a sneaker 80 or other shoe, sandal, boot, or the like and inflates the arch support cell 16 (not shown) to the desired level of inflation by pumping the hand-held pump 51 to force fluid through the connection tube 27 and inflation port 29 and into the cell 16.

Prior to applying the brace 10 as shown in FIGS. 10A-10D, the user may take a preliminary step of first positioning the cell 16 within the brace 10 so that cell 16 will fit the user's medial arch when the brace 10 is applied to the user's foot, as described above with reference to FIGS. 3A-3C where the cell 16 is positioned within the bottom portion 35 of the brace 10. The brace 10 depicted in the embodiments described herein are applicable to the left foot. But, as should be apparent based on the disclosure, the brace 10 can be readily configured for use with the right or the left foot.

The above describes exemplary embodiments of the brace as used in connection with an adjustable cell system in treating positional foot deformity. But it is to be understood that the invention is not limited to the embodiments described above. Various other implementations and embodiments are possible in view of the disclosure contained herein and should be apparent based upon a review of the disclosure. Accordingly, it is intended that the invention not be limited to the specific illustrative embodiments. All references cited herein are expressly incorporated by reference herein in their entirety and made a part of this application.

The invention claimed is:

1. A brace, comprising:
a lateral side portion and a medial side portion, the two side portions being connected by a bottom portion,
a first strap adapted to extending from the lateral side portion and beneath a foot of a user and being adapted to lift a forefoot of the user as the first strap is tightened, wherein the first strap includes a portion adapted to wrap around a heel of the user and fasten to a side section of the medial side portion, wherein the lateral side portion includes a slot defining an opening through the entire width of the lateral portion, in which the first strap is received and positioned, and
a first inflatable cell adapted to support the foot of the user, wherein the first cell is disposed within the bottom portion.

2. The brace of claim 1, wherein the first cell has at least one of air, liquid and foam.

3. The brace of claim 1, wherein the first cell is adjustably positionable within the bottom portion.

4. The brace of claim 1, wherein the first cell is adapted to be positioned along a portion of an arch of the user's foot.

5. The brace of claim 4, wherein the first cell is adapted to extend along a medial side of the user's foot above the arch.

6. The brace of claim 1, wherein the first cell is adapted to lift an instep of the user.

7. The brace of claim 1, wherein the first cell is adjustably inflatable by the user.

8. The brace of claim 7, including a pump.

9. The brace of claim 8, wherein the pump is removable and re-attachable by the user.

10. The brace of claim 8, wherein the pump is integrated with at least one of the lateral and side portions.

11. The brace of claim 1, wherein the first strap is adapted to lift a medial arch of the user's foot relative to a lateral arch of the user's foot.

12. The brace of claim 1, wherein the first strap is adapted to secure the brace against a lower leg of the user without the use of an additional strap.

13. The brace of claim 1, wherein the brace includes a housing.

14. The brace of claim 13, wherein the housing includes at least one side stiffening member.

15. The brace of claim 13, wherein the housing includes a casing.

16. The brace of claim 13, wherein the housing is adapted to receive the user's foot through a rear portion of the housing.

17. The brace of claim 13, wherein the housing is adapted to receive the user's foot through a front portion of the housing.

18. The brace of claim 1, further comprising a second strap positionable so as to connect the medial and lateral side portions.

19. The brace of claim 18, wherein the second strap is adapted to extend along a posterior region of a lower leg of the user.

20. The brace of claim 18, wherein the second strap is adapted to extend along a anterior region of a lower leg of the user.

21. The brace of claim 1, wherein at least one of the lateral and medial side portions is a rigid side wall.

22. The brace of claim 1, wherein the slot is positioned within the lateral side portion at an angle with the horizontal.

23. The brace of claim 22, wherein the angle is between approximately 10° and approximately 45°.

24. The brace of claim 1, wherein the first cell is adapted to be positioned to fit under one or more of a forefoot region, a lateral mid-foot region, and a medial arch region of the user's foot.

25. The brace of claim 1, wherein the first cell comprises a lower portion adapted to be positioned under the user's foot and an upper portion adapted to be positioned to support an upper medial arch of the user's foot.

26. The brace of claim 1, wherein the first cell is configured to be positioned around the perimeter of a medial arch of the user's foot.

27. The brace of claim 1, wherein the first cell is disposed between a lower layer and an upper layer of the bottom portion.

* * * * *